United States Patent
Lee et al.

(10) Patent No.: US 8,912,613 B2
(45) Date of Patent: Dec. 16, 2014

(54) DUAL-SIDE MICRO GAS SENSOR AND METHOD OF FABRICATING THE SAME

(71) Applicant: Electronics and Telecommunications Research Institute, Daejeon (KR)

(72) Inventors: Hyung-Kun Lee, Daejeon (KR); Seungeon Moon, Daejeon (KR); Nak Jin Choi, Daejeon (KR); Jaewoo Lee, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 0 days.

(21) Appl. No.: 13/909,477

(22) Filed: Jun. 4, 2013

(65) Prior Publication Data

US 2014/0175570 A1    Jun. 26, 2014

(30) Foreign Application Priority Data

Dec. 24, 2012    (KR) .................. 10-2012-0152405

(51) Int. Cl.
*H01L 27/14* (2006.01)
*G01N 27/12* (2006.01)

(52) U.S. Cl.
CPC ............ *G01N 27/128* (2013.01); *G01N 27/123* (2013.01)
USPC ........... 257/414; 257/415; 257/416; 257/417; 257/419; 257/420

(58) Field of Classification Search
USPC .................. 257/414, 415, 416, 417, 419, 420
See application file for complete search history.

(56) References Cited

U.S. PATENT DOCUMENTS

| | | | |
|---|---|---|---|
| 4,706,493 A | 11/1987 | Chang et al. | |
| 7,452,126 B2 | 11/2008 | Arndt et al. | |
| 2010/0170888 A1* | 7/2010 | Lee et al. | ............ 219/542 |
| 2014/0105790 A1* | 4/2014 | Gaudon et al. | ............ 422/90 |

FOREIGN PATENT DOCUMENTS

| | | |
|---|---|---|
| KR | 10-2005-0051884 B1 | 6/2005 |
| KR | 10-2009-0059792 B1 | 6/2009 |

* cited by examiner

*Primary Examiner* — Tan N Tran (57) ABSTRACT

Provided are a dual-side micro gas sensor and a method of fabricating the same. The sensor may include an elastic layer, a heat-generating resistor layer on the elastic layer, an interlayered insulating layer on the heat-generating resistor layer, an upper sensing layer on the interlayered insulating layer, and a lower sensing layer provided below the elastic layer to face the heat-generating resistor layer, thereby reducing heat loss of the heat-generating resistor layer.

9 Claims, 9 Drawing Sheets

DUAL-SIDE MICRO GAS SENSOR AND METHOD OF FABRICATING THE SAME

CROSS-REFERENCE TO RELATED APPLICATIONS

This U.S. non-provisional patent application claims priority under 35 U.S.C. §119 to Korean Patent Application No. 10-2012-0152405, filed on Dec. 24, 2012, in the Korean Intellectual Property Office, the entire contents of which are hereby incorporated by reference.

BACKGROUND OF THE INVENTION

Example embodiments of the inventive concept relate to a dual-side micro gas sensor and a method of fabricating the same.

Recently, micro sensors and micro heating devices have been developed with the advance of semiconductor technology. Especially, there is an increasing interest on semiconductor gas sensors, because the semiconductor gas sensor has high sensitivity and is able to be manufactured with a low cost. However, the semiconductor gas sensor suffers from low thermal efficiency. In detail, a heating device is needed for a gas sensor, and thus, the gas sensor suffers from high power consumption. Accordingly, the gas sensor has not been used for power-limited applications, such as mobile devices (e.g., cellular phone) or wireless sensor nodes. In this sense, there are many researches on a gas sensor with a low power heating element.

A conventional micro gas sensor may be a single-side micro gas sensor. The single-side micro gas sensor includes a heat-generating resistor layer on a substrate and a sensing layer on the heat-generating resistor layer. The sensing layer may be heated by the heat-generating resistor to be activated. However, the single-side micro gas sensor suffers from low thermal efficiency of the heat-generating resistor.

SUMMARY

Example embodiments of the inventive concept provide a dual-side micro gas sensor with high thermal efficiency.

According to example embodiments of the inventive concepts, a dual-side micro gas sensor may include an elastic layer, a heat-generating resistor layer on the elastic layer, an interlayered insulating layer on the heat-generating resistor layer, an upper sensing layer on the interlayered insulating layer, and a lower sensing layer provided below the elastic layer to face the heat-generating resistor layer, the lower sensing layer reducing heat loss of the heat-generating resistor layer.

In example embodiments, the dual-side micro gas sensor may further include a substrate provided on a bottom surface of the elastic layer to support the elastic layer and have an opening exposing the lower sensor.

In example embodiments, the dual-side micro gas sensor may further include upper electrodes disposed between the upper sensing layer and the interlayered insulating layer, and lower electrodes disposed between the lower sensing layer and the elastic layer. The lower electrodes and the lower sensing layer may be provided in the opening of the substrate. The upper electrodes may include a first upper electrode and a second upper electrode that is spaced apart from the first upper electrode.

In example embodiments, the lower electrodes may include a first lower electrode and a second lower electrode that is spaced apart from the first lower electrode.

In example embodiments, the upper sensing layer and the lower sensing layer may include at least one of metal oxide, metal nano particles, quantum dots, conductive polymer, carbon nanotube, or graphene.

In example embodiments, the elastic layer may include a silicon oxide layer and a silicon nitride layer.

In example embodiments, the heat-generating resistor layer may include at least one of metals or metal oxides.

According to example embodiments of the inventive concepts, a method of fabricating a dual-side micro gas sensor may include forming a lower electrode on a substrate, forming an elastic layer on the lower electrode and the substrate, forming a heat-generating resistor layer on the elastic layer, forming an interlayered insulating layer on the heat-generating resistor layer, forming an upper electrode on the interlayered insulating layer, forming an upper sensing layer on the upper electrode and the interlayered insulating layer, etching a portion of the substrate to form an opening exposing the lower electrode, and forming a lower sensing layer in the opening to cover the lower electrode and the elastic layer.

In example embodiments, the forming of the lower electrode may include forming a trench on the substrate, and forming the lower electrode in the trench.

In example embodiments, the upper sensing layer and the lower sensing layer may be formed using at least one of screen printing, inkjet printing, electro-hydrodynamic printing, thermal deposition, e-beam deposition, sol-gel, drop-coating, or chemical vapor deposition methods.

In example embodiments, the elastic layer may be formed using a chemical vapor deposition process.

BRIEF DESCRIPTION OF THE DRAWINGS

Example embodiments will be more clearly understood from the following brief description taken in conjunction with the accompanying drawings. The accompanying drawings represent non-limiting, example embodiments as described herein.

It should be noted that these figures are intended to illustrate the general characteristics of methods, structure and/or materials utilized in certain example embodiments and to supplement the written description provided below. These drawings are not, however, to scale and may not precisely reflect the precise structural or performance characteristics of any given embodiment, and should not be interpreted as defining or limiting the range of values or properties encompassed by example embodiments. For example, the relative thicknesses and positioning of molecules, layers, regions and/or structural elements may be reduced or exaggerated for clarity. The use of similar or identical reference numbers in the various drawings is intended to indicate the presence of a similar or identical element or feature.

DETAILED DESCRIPTION

Example embodiments of the inventive concepts will now be described more fully with reference to the accompanying drawings, in which example embodiments are shown. Example embodiments of the inventive concepts may, however, be embodied in many different forms and should not be construed as being limited to the embodiments set forth herein; rather, these embodiments are provided so that this disclosure will be thorough and complete, and will fully convey the concept of example embodiments to those of ordinary skill in the art. In the drawings, the thicknesses of layers and regions are exaggerated for clarity. Like reference numerals in the drawings denote like elements, and thus their description will be omitted.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Like numbers indicate like elements throughout. As used herein the term "and/or" includes any and all combinations of one or more of the associated listed items. Other words used to describe the relationship between elements or layers should be interpreted in a like fashion (e.g., "between" versus "directly between," "adjacent" versus "directly adjacent," "on" versus "directly on").

It will be understood that, although the terms "first", "second", etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of example embodiments.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises", "comprising", "includes" and/or "including," if used herein, specify the presence of stated features, integers, steps, operations, elements and/or components, but do not preclude the presence or addition of one or more other features, integers, steps, operations, elements, components and/or groups thereof.

Example embodiments of the inventive concepts are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments of the inventive concepts should not be construed as limited to the particular shapes of regions illustrated herein but are to include deviations in shapes that result, for example, from manufacturing. For example, an implanted region illustrated as a rectangle may have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments of the inventive concepts belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

Figure 1:
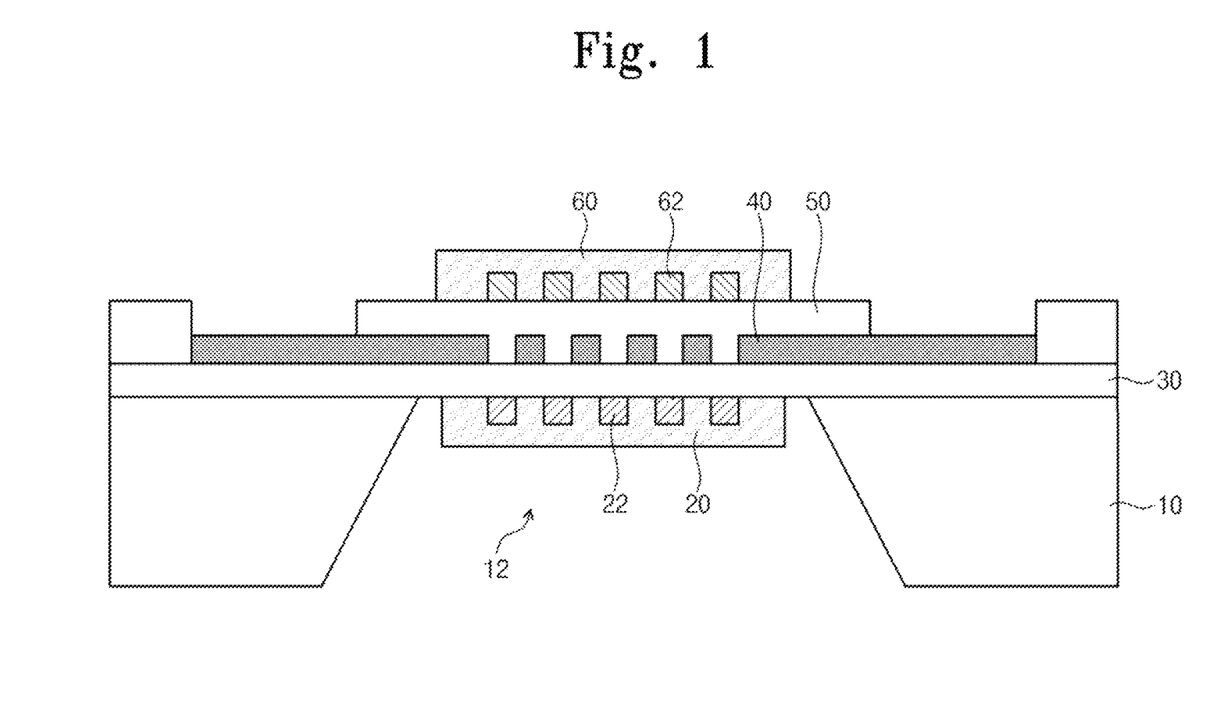
FIGS. 1 and 2 are sectional and perspective views illustrating a dual-side micro gas sensor according to example embodiments of the inventive concept.
Figure 2:
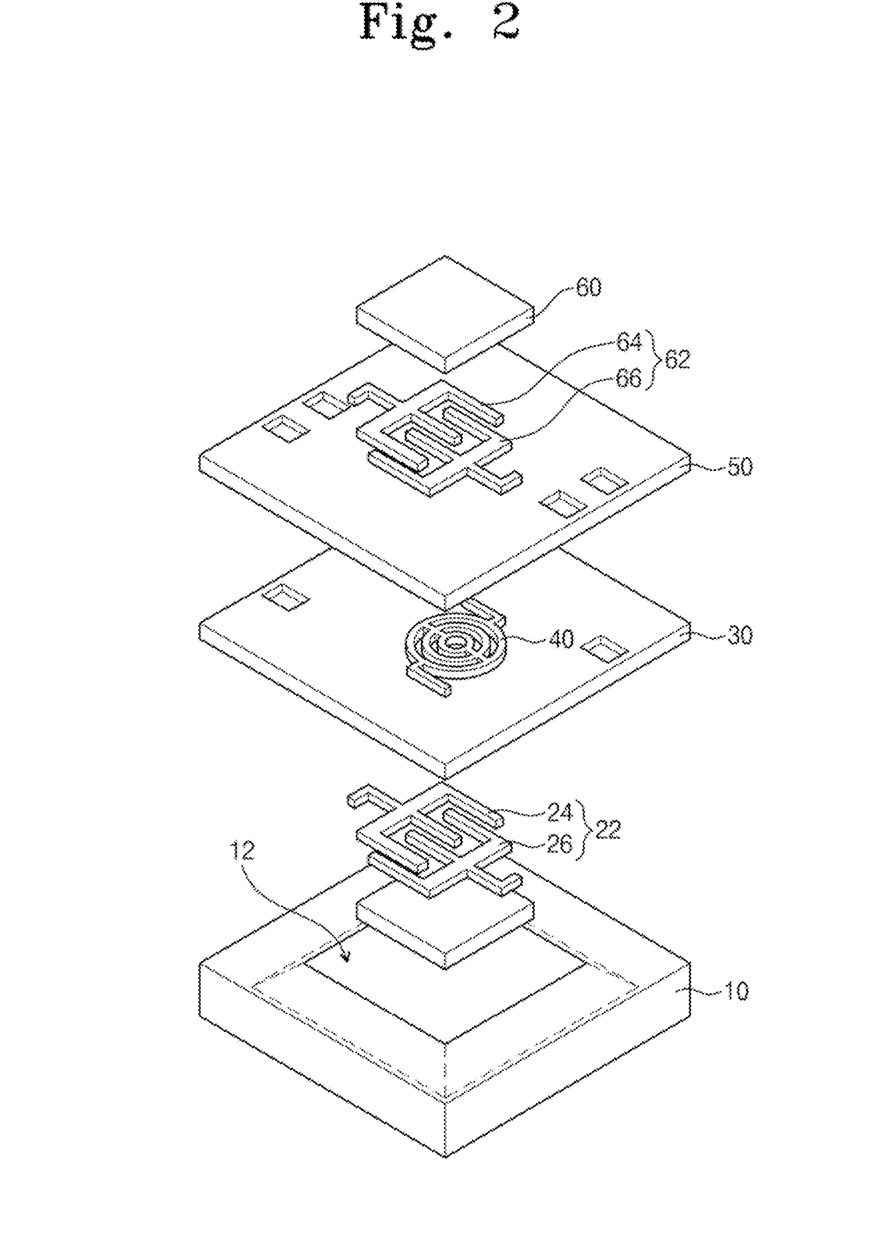

FIGS. 1 and 2 are sectional and perspective views illustrating a dual-side micro gas sensor according to example embodiments of the inventive concept.

Referring to FIGS. 1 and 2, a dual-side micro gas sensor may include a substrate 10, a lower sensing layer 20, a lower electrode 22, an elastic layer 30, a heat-generating resistor layer 40, an interlayered insulating layer 50, an upper electrode 62, and an upper sensing layer 60.

The substrate 10 may be provided to have an opening 12. The substrate 10 may include a crystalline silicon layer. The opening 12 may be formed to expose the lower sensing layer 20.

The lower sensing layer 20 and the lower electrodes 22 may be provided in the opening 12. The lower sensing layer 20 may include at least one of metal oxide, metal nano particles, quantum dots, conductive polymer, carbon nanotube, or graphene. The lower electrodes 22 may include at least one of metals (e.g., platinum or aluminum) or metal oxides. The lower electrodes 22 may include a first lower electrode 24 and a second lower electrode 26. The first lower electrode 24 and the second lower electrode 26 may be provided spaced apart from each other. The lower sensing layer 20 may be disposed between the first lower electrode 24 and the second lower electrode 26.

The elastic layer 30 may be provided on the substrate 10. The lower sensing layer 20 and the lower electrode 22 may be supported by the elastic layer 30. The elastic layer 30 may include a silicon oxide layer and a silicon nitride layer. In example embodiments, the elastic layer 30 may include, for example, a first silicon oxide layer, a first silicon nitride layer, and a second silicon oxide layer.

The heat-generating resistor layer 40 and the interlayered insulating layer 50 may be provided on the elastic layer 30. The heat-generating resistor layer 40 may be configured to be heated up to a temperature of about 500° C. by an external power voltage. The heat-generating resistor layer 40 may include at least one of polysilicon, tungsten, aluminum, nickel, or platinum.

The interlayered insulating layer 50 may be provided on the heat-generating resistor layer 40 and the elastic layer 30. The interlayered insulating layer 50 may include silicon oxide.

The upper electrodes 62 and the upper sensing layer 60 may be provided on the interlayered insulating layer 50. The upper electrodes 62 may include a first upper electrode 64 and a second upper electrode 66. The upper sensing layer 60 may be disposed between the first upper electrode 64 and the second upper electrode 66. The upper electrodes 62 may include metal. The upper sensing layer 60 may include at least one of metal oxide, metal nano particles, quantum dots, conductive polymer, carbon nanotube, or graphene. In example embodiments, the lower sensing layer 20 and the upper sensing layer 60 may be configured to be activated at a high temperature (e.g., of about 200-400° C.). The heat-generating resistor layer 40 may be configured to heat the lower sensing layer 20 and the upper sensing layer 60 to the activation temperature. The lower sensing layer 20 may improve gas sensing efficiency. The lower sensing layer 20 may be configured to reduce a heat loss thereof.

According to example embodiments of the inventive concept, the dual-side micro gas sensor may be configured to have an increased thermal efficiency.

The dual-side micro gas sensor may be fabricated by a method to be described below.

FIGS. 3 through 11 are sectional views illustrating a process of fabricating the dual-side micro gas sensor of FIG. 1.

Figure 3:
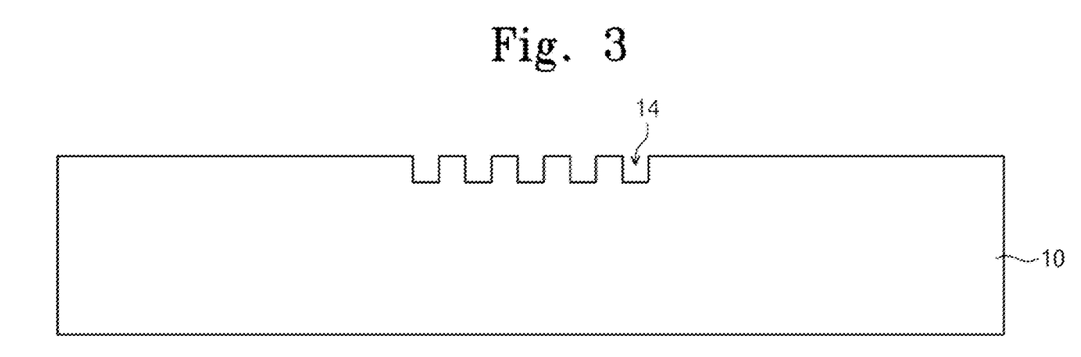
FIGS. 3 through 11 are sectional views illustrating a process of fabricating the dual-side micro gas sensor of FIG. 1.

Referring to FIG. 3, a trench 14 may be formed on the substrate 10. The trench 14 may be formed by performing a photolithography process and an etching process.

Figure 4:
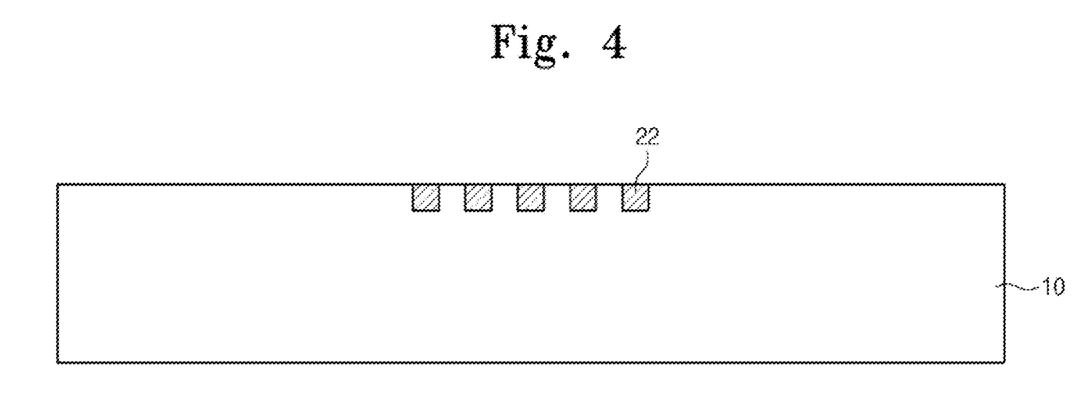

Referring to FIG. 4, the lower electrodes 22 may be formed in the trench 14. The formation of the lower electrodes 22 may include depositing a metal layer on the substrate 10 with the trench 14 and performing a chemical mechanical polishing process to the metal layer. The deposition of the metal layer may be performed using a sputtering process or a chemical vapor deposition process. As the result of the chemical mechanical polishing process, the lower electrodes 22 remaining in the trench 14 may have a flat top surface.

Figure 5:
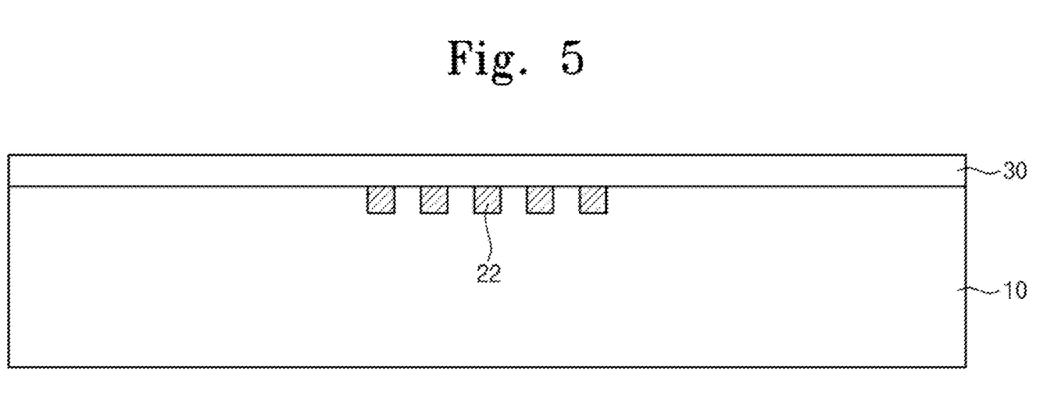

Referring to FIG. 5, the elastic layer 30 may be formed on the lower electrodes 22 and the substrate 10. The elastic layer 30 may be formed to have a multi-layered structure including a silicon oxide layer and a silicon nitride layer stacked on the substrate 10. Each or all of the silicon oxide layer and the silicon nitride layer may be formed using a chemical vapor deposition process.

Figure 6:
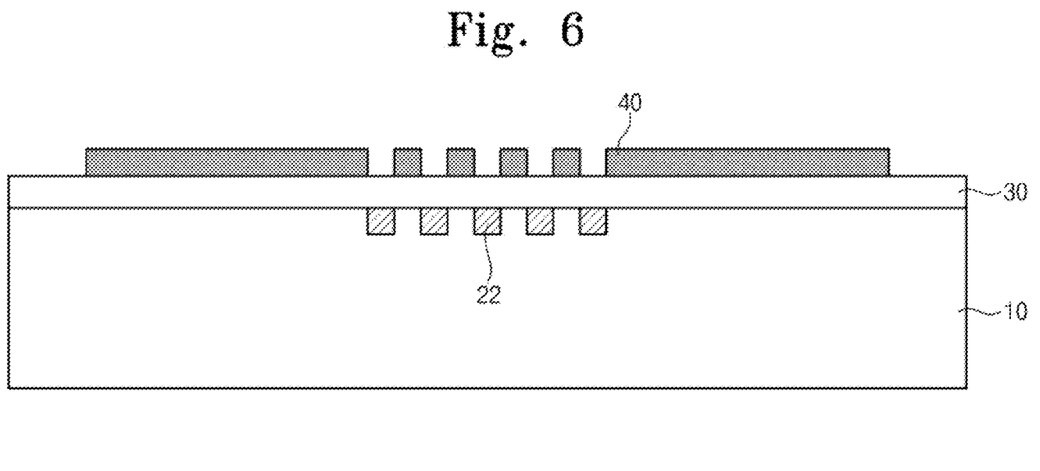

Referring to FIG. 6, the heat-generating resistor layer 40 may be formed on the elastic layer 30. The heat-generating resistor layer 40 may be formed by performing a metal deposition process, a photolithography process, and an etching process.

Figure 7:
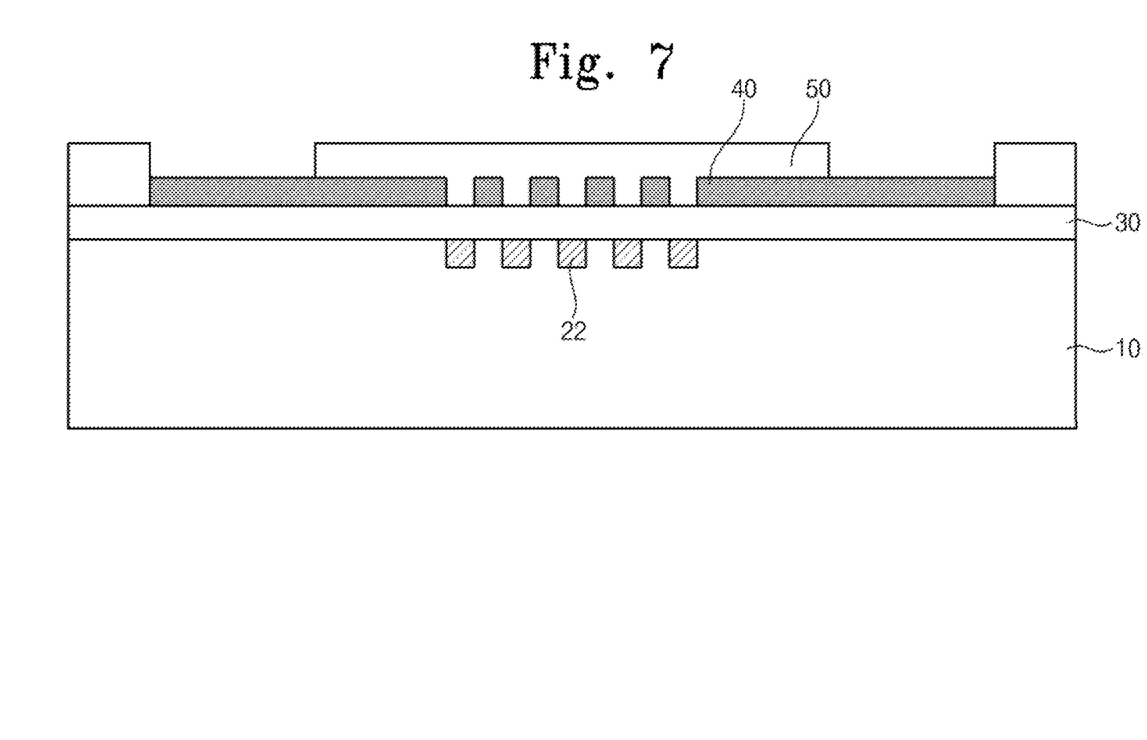

Referring to FIG. 7, the interlayered insulating layer 50 may be formed on the heat-generating resistor layer 40 and the elastic layer 30. The interlayered insulating layer 50 may include a silicon oxide layer, which may be formed by a chemical vapor deposition process. The interlayered insulating layer 50 may be patterned by a photolithography process and an etching process.

Figure 8:
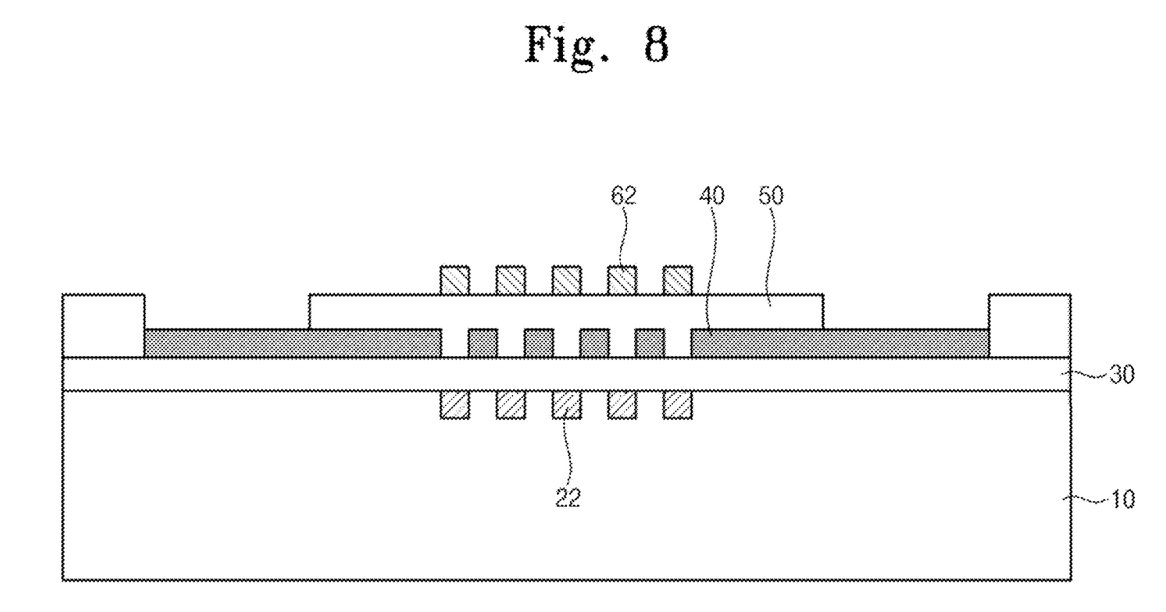

Referring to FIG. 8, the upper electrodes 62 may be formed on the interlayered insulating layer 50. The upper electrodes 62 may be formed by performing a metal deposition process, a photolithography process, and an etching process.

Figure 9:
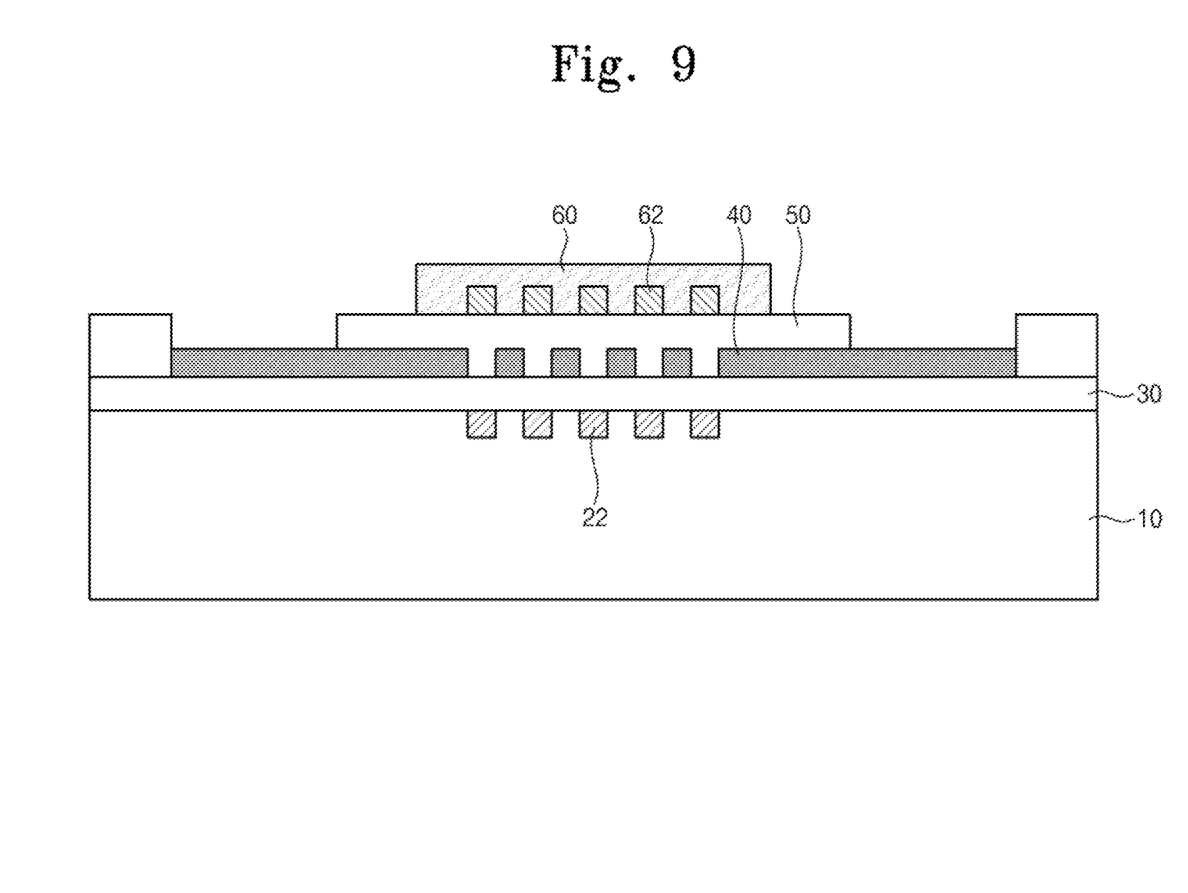

Referring to FIG. 9, the upper sensing layer 60 may be formed on the upper electrodes 62 and the interlayered insulating layer 50. The upper sensing layer 60 may be formed using at least one of screen printing, inkjet printing, electro-hydrodynamic printing, thermal deposition, e-beam deposition, sol-gel, drop-coating, or chemical vapor deposition methods.

Figure 10:
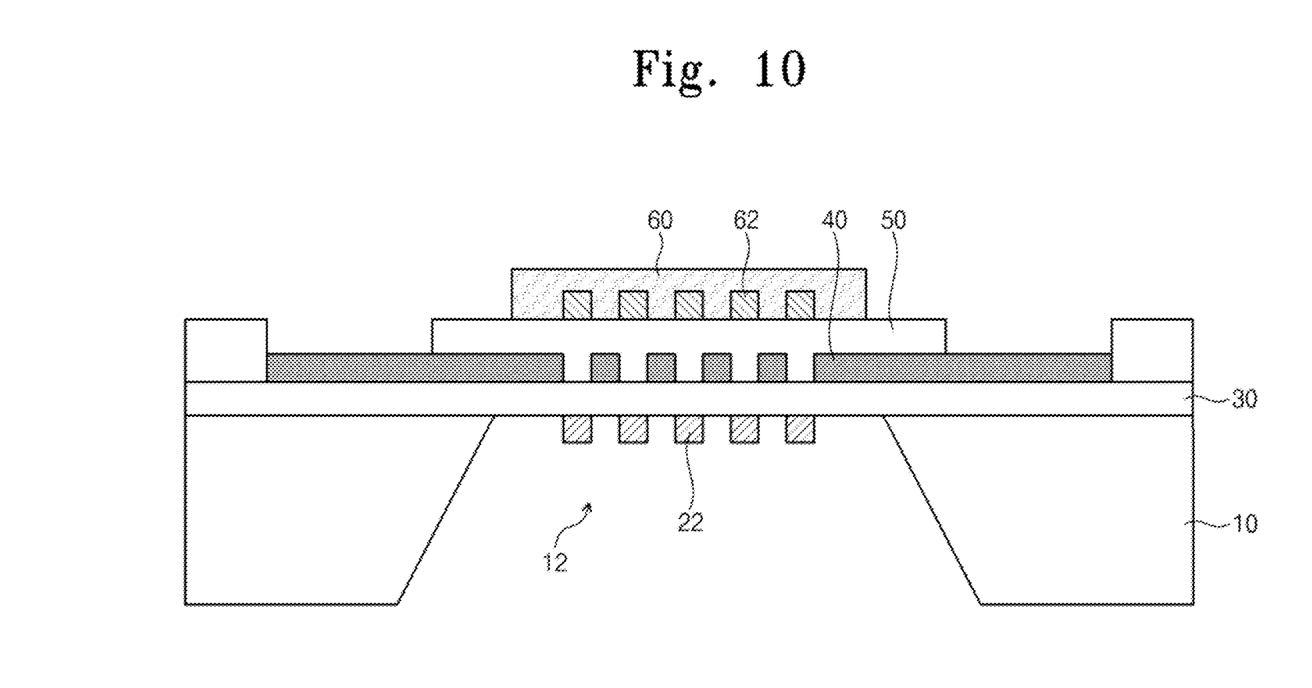

Referring to FIG. 10, a portion of the substrate 10 may be removed to form the opening 12 exposing the lower electrodes 22. The opening 12 may be formed by performing a photolithography process and an etching process.

Figure 11:
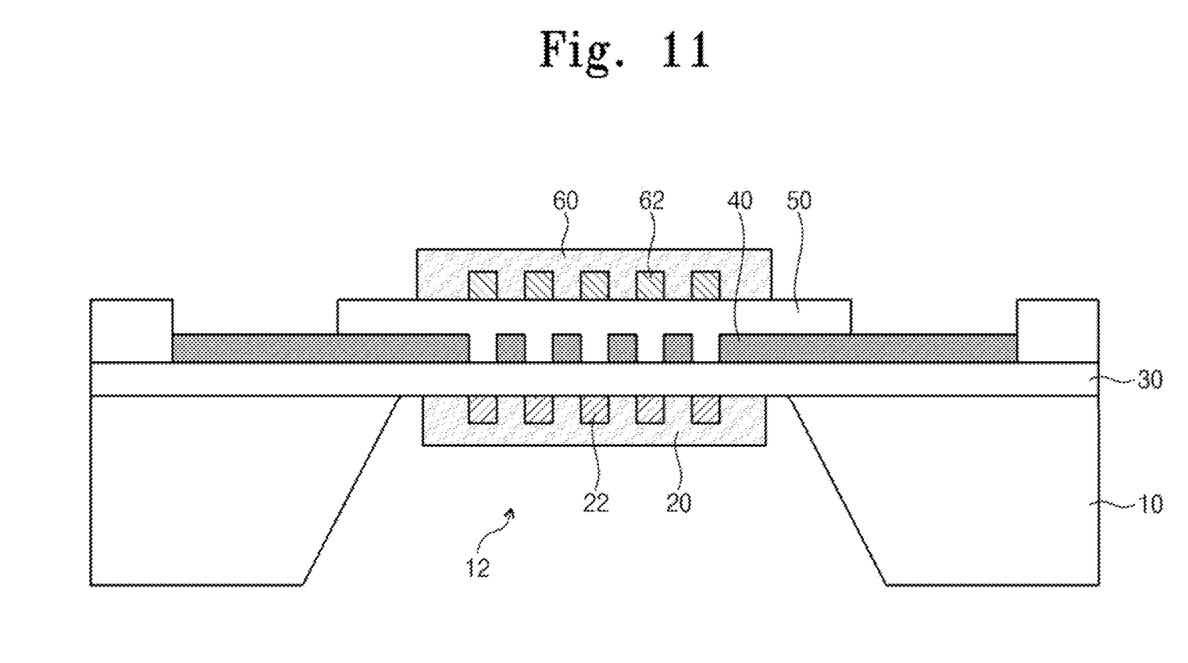

Referring to FIG. 11, the lower sensing layer 20 may be formed in the opening 12 to cover the lower electrodes 22 and the elastic layer 30. The lower sensing layer 60 may be formed using at least one of screen printing, inkjet printing, electro-hydrodynamic printing, thermal deposition, e-beam deposition, sol-gel, drop-coating, or chemical vapor deposition methods.

According to example embodiments of the inventive concept, the dual-side micro gas sensor may include the lower sensing layer, the elastic layer, the heat-generating resistor layer, the interlayered insulating layer, and the upper sensing layer. The heat-generating resistor layer may be provided between the upper sensing layer and the lower sensing layer. The upper sensing layer and the lower sensing layer may be configured to be activated by an external gas in a high temperature. The heat-generating resistor layer may be configured to heat the upper sensing layer and the lower sensing layer to a high temperature. The upper sensing layer and the lower sensing layer may be configured to reduce heat loss of the heat-generating resistor layer.

Accordingly, it is possible to improve thermal efficiency of the dual-side micro gas sensor according to example embodiments of the inventive concept.

While example embodiments of the inventive concepts have been particularly shown and described, it will be understood by one of ordinary skill in the art that variations in form and detail may be made therein without departing from the spirit and scope of the attached claims.

What is claimed is:

1. A dual-side micro gas sensor, comprising:
    an elastic layer;
    a heat-generating resistor layer disposed on the elastic layer;
    an interlayer insulating layer disposed on the heat-generating resistor layer;
    an upper sensing layer disposed on the interlayer insulating layer; and
    a lower sensing layer attached directly to a bottom surface of the elastic layer such that it receives heat from the heat-generating resistor layer,
    wherein the heat-generating layer is the only heat source for the upper sensing layer and the lower sensing layer.

2. The dual-side micro gas sensor of claim 1, further comprising a substrate provided on a bottom surface of the elastic layer, the substrate supporting the elastic layer and having an opening exposing the lower sensor.

3. The dual-side micro gas sensor of claim 2, further comprising:
    upper electrodes disposed between the upper sensing layer and the interlayer insulating layer; and
    lower electrodes disposed between the lower sensing layer and the elastic layer.

4. The dual-side micro gas sensor of claim 3, wherein the lower electrodes and the lower sensing layer are provided in the opening of the substrate.

5. The dual-side micro gas sensor of claim 3, wherein the upper electrodes comprise a first upper electrode and a second upper electrode that is spaced apart from the first upper electrode.

6. The dual-side micro gas sensor of claim 3, wherein the lower electrodes comprise a first lower electrode and a second lower electrode that is spaced apart from the first lower electrode.

7. The dual-side micro gas sensor of claim 1, wherein the upper sensing layer and the lower sensing layer comprise at least one of metal oxide, metal nano particles, quantum dots, conductive polymer, carbon nanotube, or graphene.

8. The dual-side micro gas sensor of claim 1, wherein the elastic layer comprises a silicon oxide layer and a silicon nitride layer.

9. The dual-side micro gas sensor of claim 1, wherein the heat-generating resistor layer comprises at least one of a metal or a metal oxide.

* * * * *